United States Patent [19]
Avalle

[11] Patent Number: 6,004,541
[45] Date of Patent: Dec. 21, 1999

[54] PERFLUORIDATED-DERIVATIVES COVERED POWDER FOR PROTECTIVE PRODUCTS AGAINST UV RAYS, PARTICULARLY FOR COSMETIC PRODUCTS

[75] Inventor: Nadia Avalle, Milan, Italy

[73] Assignee: Intercos Italia S.p.A., Milan, Italy

[21] Appl. No.: 09/109,184

[22] Filed: Jul. 2, 1998

[30] Foreign Application Priority Data

Jul. 7, 1997 [IT] Italy ................................. MI97A1602

[51] Int. Cl.⁶ ................ A61K 7/42; A61K 7/44; A61K 7/035
[52] U.S. Cl. ................ 424/59; 424/60; 424/69; 424/400; 424/401
[58] Field of Search ................ 424/59, 66, 69, 424/400, 401

[56] References Cited

U.S. PATENT DOCUMENTS

| | | | |
|---|---|---|---|
| 5,741,518 | 4/1998 | Ribier et al. | 424/450 |
| 5,851,539 | 12/1998 | Mellul et al. | 424/401 |
| 5,866,158 | 2/1999 | Ribier et al. | 424/450 |

*Primary Examiner*—Shelley A. Dodson
*Attorney, Agent, or Firm*—Jacobson, Price, Holman & Stern, PLLC

[57] ABSTRACT

A powder for use in products which boast a protective factor against sunbeams or UV rays includes the following ingredients:

a) 0.1–99.99% of a powder phase;
b) 0.01–10% of a perfluoridated-derivatives phase;
c) 0–5% of an agent coupling phases a) and b).

The powder is particularly suitable for cosmetic products, particularly for make-up products.

7 Claims, No Drawings

PERFLUORIDATED-DERIVATIVES COVERED POWDER FOR PROTECTIVE PRODUCTS AGAINST UV RAYS, PARTICULARLY FOR COSMETIC PRODUCTS

The present invention relates to a perfluoridated-derivatives covered powder for products which boasts protection against sunbeams or UV rays, particularly for cosmetic products.

Employment of inorganic powders as ingredients able to absorb or diffract sunbeams or UV radiations and to protect the substrate on which they are applied so as to reduce the damage that such radiations can perform, is known in the art. A common example of such an employment is in cosmetic products, especially those that claim some sun protection factor SPF. In these cosmetic products, besides chemical filters, that is substances able to absorb U. V. rays due to their chemical structure, or instead of them, the so called inorganic or physical filters, which in point of fact prevent U.V. rays passage due to their own particle dimension, are commonly used.

Although all powders show some shielding efficacy, in point of fact titanium dioxide and zinc oxide are the most useful and commonly employed as inorganic filters powders.

A particular effectiveness is given by the so called "ultrafine" forms, in which the particle dimension decreases below 100 nanometer up to 15–40 nanometer average values.

Ultrafine powders are already present in every make-up cosmetics, such as for example foundation, fard, eye shadow, lipsticks and so on, which are employed in coloring skin and lips and are mostly composed by inorganic powders. By applying these products on the skin a dyed film is made which masks skin defects and give it visually a more uniform look. This film is commonly able to perform an intermediate-low sun protection factor, even without specific powders such as titanium dioxide and zinc oxide.

According to this invention it has been now surprisingly discovered that the powder covering with perfluoridated ingredients allow to improve powder capacity in protecting against sunbeams or ultraviolets, lowering the powder type and/or dimension limitations. In other words, by employing perfluoridated-ingredients covered powders excellent protection results are achieved also with powders different from titanium dioxide and zinc oxide, and anyway also with non "ultrafine" powders.

In particular such perfluoridated-ingredients covered powders are able to be used in cosmetic products which boast protective effects from sunbeams or UV rays, preferably in cosmetic make-up products which boast protective effects from sunbeams and/or UV rays, more preferably in cosmetic make-up products in compact powder or compact which claim protective effects from sunbeams and/or UV rays.

According to the invention a perfluoridated-derivatives covered powder is characterized in that it comprises the following ingredients:

a) 0.1–99.99% of a powder phase;

b) 0.01–10% of a perfluoridated-derivatives phase;

c) 0–5% of an agent coupling the two phases a) and b).

The powder phase may be consisting of various excipients traditionally used in cosmetics: talc, mica, kaolin, starch, zinc oxide, (ultrafine or not), nylon 12, polyethylene, silica, globular silica, acrylate polymers and copolymers, and so on, alone or mixed among them or in combination with pigments such as iron oxide, chrome oxide, chrome hydroxide, ultramarine blue, ultramarine pink, manganese violet, titanium dioxide (ultrafine or not), mica and titanium dioxide based pellets, mica and bismuth oxychloride based pellets, carmine, organic dyes based lacquers and pigments as from CTFA.

The perfluoridated-ingredients phase may be constituted by different substances having in their molecular structure fluorine atoms bonded directly to carbon ones. Examples of such products are: perfluoripolymethyl isopropylethere, perfluoripolymethyl isopropylethere phosphate acid or salt thereof, perfluorialkylphosphate acid or salt thereof, and so on. The perfluoridated product percentage on powder ranges from 0.01 to 10%, preferably from 0.5 to 5%, more preferably from 1 to 4%.

This phase may be bonded to the powders by a water soluble metallic salt. Examples of such salts are Al, Mg, Ca, Zn, Zr, and Ti soluble salts.

Some example of powders treated with perfluoridated ingredients are products marketed with Covafluor trademark by Les Colourants Wackherr, or FT marked treated powders of U.S. Cosmetics Corporation.

Alternatively and preferably such powders may be prepared according to one of the treatment methods disclosed in examples 1 to 4, hereinafter:

EXAMPLE 1

970 g of red iron oxide pretreated with 30 weight % of mica, suspended in a Cazzola stirrer (3000 rpm/min.), were added to 60 g of a 50 weight % of Fomblin HC/P2 solution in EtOH, nebulizing. Product was dried in oven at 80° C. and riddled at 200 mesh.

EXAMPLE 2

1477 g of talc maintained in suspension in a Cazzola stirrer (3000 rpm/min.), were added to 115 g of a 13 weight % of $Al_2(SO_4)_3$ aqueous solution, nebulizing. Subsequently 112 g of a 20 weight % of Fomblin hydroalcoholic solution pH=9, without interrupting processing, were nebulized. The product was dried in oven at 80° C. under vacuum and riddled at 200 mesh.

EXAMPLE 3

97 g of yellow iron oxide and 15 g of a 20 weight % of Fomblin HC/P2 hydroalcoholic solution pH =9 were added to 200 g of deionized water under mechanic stirring. Mixture was let react for 15' until an homogeneous dispersion is obtained. 2.52 g of $Al_2(SO_4)_3$ presolubilized in 30 ml of water, were slowly added to the solution. Once the addition was ended, the system was let react for 15', filtered under vacuum, dried in oven at 80° C., and riddled at 200 mesh.

EXAMPLE 4

970 g of titanium dioxide were slowly added to 2.5 kg of a 1.2 weight % of Fomblin HC/P2 alcoholic solution. The mixture was let react for 20', dried in oven at 70° C., milled and riddled at 200 mesh.

According to the invention, with such covered powders a composition for make-up cosmetic protective product may be provided which is characterized in that it employs the following ingredients:

a) 0.1–99.9% of a treated or perfluoridated-derivatives covered powder phase, as above defined;

b) 0.1–99.9% of other cosmetically acceptable components.

The composition of this invention provides use of 0.1–99.99% of other cosmetically acceptable components such as oils, waxes, surfactants, silicones, other non- or otherwise covered powders, perfumes, dyestuffs, or colored pigments, or other raw materials as from CTFA.

FORMULATION EXAMPLES

EXAMPLE 5
Pressed Cosmetic Powder

Some variants of a foundation formulation in compact powder shown in the following table were prepared, which were measured for sun protection factor (SPF), according to Colipa described proceedings.

| Formulations | A | B | C | D | E | F | G | H |
|---|---|---|---|---|---|---|---|---|
| Talc | 75 | — | — | 75 | — | 75 | — | 76.5 |
| Mica | 10 | — | — | 10 | — | 10 | 10 | 10 |
| Titanium dioxide/Mica (70/30) | 1.5 | — | — | — | — | — | — | — |
| Iron Oxides/Mica (70/30) | 7 | — | — | 7 | — | 7 | 7 | 7 |
| Talc treated as in ex. 1 | — | 75 | 76.5 | — | 58.5 | — | — | — |
| Mica treated as in ex. 1 | — | 10 | 10 | — | 10 | — | — | — |
| Titanium dioxide/Mica (70/30) treated as in ex. 1 | — | 1.5 | — | 1.5 | 18 | — | — | — |
| Iron oxides/Mica (70/30) treated as in ex. 1 | — | 7 | 7 | — | 7 | — | — | — |
| Preservative | 0.5 | 0.5 | 0.5 | 0.5 | 0.5 | 0.5 | 0.5 | 0.5 |
| Magnesium stearate | 2 | 2 | 2 | 2 | 2 | 2 | 2 | 2 |
| Mineral oil | 1.5 | 1.5 | 1.5 | 1.5 | 1.5 | 1.5 | 1.5 | 1.5 |
| Octyl-dodecyl-stearyl stearate | 2.5 | 2.5 | 2.5 | 2.5 | 2.5 | 2.5 | 2.5 | 2.5 |
| $TiO_2$ FT ULTRAFLUORIDE | | | | | | 1.5 | — | |
| Talc J13 FT ULTRAFLUORIDE | | | | | | — | 76.5 | |
| SPF values | 4.3 | 15 | 12.5 | 6.3 | 26 | 6.2 | 13 | 3.2 |

The table shows that by comparing formulation A, without perfluoridated products, with formulation B, where the powders were covered by Fomblin HC/P2, an excellent sun protection improvement is obtained. SPF value improves also in formulations without titanium dioxide (formulation H) if the powders were covered by Fomblin HC/P2 or others perfluoridates (formulation G). When titanium dioxide is present (formulation A), SPF value improves if it was covered by Fomblin HC/P2 (formulation D) or others perfluoridates (formulation F) and further improves by increasing concentration (formulation E).

EXAMPLE 6

A foundation in emulsion according to the following formulation was prepared by using powders and pigments covered by the same process of example 1. Also in this case, a protection factor improvement, due to covered pigments presence, is evident.

| | | |
|---|---|---|
| Titanium dioxide/Mica(70/30) covered as in ex. 1 | | 12.7 |
| Iron oxides/Mica(70/30) covered as in ex. 1 | | 2.2 |
| Titanium dioxide/Mica(70/30) | 12.7 | — |
| Iron Oxides/Mica(70/30) | 2.2 | — |
| Water | 51 | 51 |
| Thickeners | 1.1 | 1.1 |
| Silicones | 16 | 16 |
| Active ingredients complex | 0.4 | 0.4 |
| Emulsifier | 8 | 8 |
| Dampenings | 7.4 | 7.4 |
| NaOH | 0.2 | 0.2 |
| Preservatives | 1 | 1 |
| SPF VALUES | 10 | 21 |

I claim:

1. Powder for products which boast protection against sunbeams or UV rays, comprising the following ingredients:

a) 0.1–99.99% of a powder phase;

b) 0.01–10% of a perfluoridated-ingredients phase;

c) 0–5% of an agent coupling the two phases a) and b), wherein the coupling agent is at least one metallic salt, and the salt is water soluble.

2. Cosmetic composition which boast protection against sunbeams or UV rays, containing one or more powders according to claim 1, comprising cosmetically acceptable components in the following percentages:

a) 0.1–99.9% of the powder phase;

b) 0.1–99.9% of other cosmetically acceptable components.

3. Make-up cosmetic composition which boast protection against sunbeams or UV rays, containing one or more powders according to claim 1, comprising cosmetically acceptable components in the following percentages:

a) 0.1–99.9% of the powder phase;

b) 0.1–99.9% of other cosmetically acceptable components.

4. The powder according to claim 1, wherein the coupling agent is selected from the group consisting of soluble salts of Al, Mg, Ca, Zn, Zr, and Ti.

5. The powder according to claim 1, wherein the perfluoridated-ingredients phase consists essentially of one or more perfluoridated compounds, and the perfluoridated compounds are selected from the group consisting of perfluoripolymethyl isopropylethere, perfluoripolymethyl isopropylethere phosphate acid, perfluoripolymethyl isopropylethere phosphate salt, perfluorialkylphosphate acid, and perfluorialkylphosphate salt.

6. The powder according to claim 1, wherein the perfluoridated-ingredients phase ranges from 0.5 to 5% of the powder.

7. The powder according to claim 6, wherein the perfluoridated-ingredients phase ranges from 1 to 4% of the powder.

* * * * *